United States Patent [19]

Viklund

[11] Patent Number: 5,573,535
[45] Date of Patent: Nov. 12, 1996

[54] BIPOLAR SURGICAL INSTRUMENT FOR COAGULATION AND CUTTING

[75] Inventor: Mark C. Viklund, New Milford, Conn.

[73] Assignee: United States Surgical Corporation, Norwalk, Conn.

[21] Appl. No.: 311,072

[22] Filed: Sep. 23, 1994

[51] Int. Cl.⁶ .................................................. A61B 17/39
[52] U.S. Cl. ............................... 606/51; 606/52; 606/41; 606/37
[58] Field of Search ............................ 606/37–41, 45–52, 606/205–208

[56] References Cited

U.S. PATENT DOCUMENTS

| | | |
|---|---|---|
| 2,031,682 | 2/1936 | Wappler et al. ........................ 606/51 |
| 3,643,663 | 2/1972 | Sutter . |
| 3,920,021 | 11/1975 | Hiltebrandt . |
| 3,938,527 | 2/1976 | Rioux et al. . |
| 4,003,380 | 1/1977 | Wien . |
| 4,005,714 | 2/1977 | Hiltebrandt . |
| 4,016,881 | 4/1977 | Rioux et al. . |
| 4,076,028 | 2/1978 | Simmons . |
| 4,202,337 | 5/1980 | Hren et al. . |
| 4,228,800 | 10/1980 | Degler, Jr. et al. . |
| 4,311,145 | 1/1982 | Esty et al. . |
| 4,418,692 | 12/1983 | Guay . |
| 4,655,216 | 4/1987 | Tischer . |
| 4,674,499 | 6/1987 | Pao . |
| 4,732,149 | 3/1988 | Sutter . |
| 4,823,791 | 4/1989 | D'Amelio et al. . |
| 4,890,610 | 1/1990 | Kirwan, Sr. et al. . |
| 4,985,030 | 1/1991 | Melzer et al. . |
| 5,171,311 | 12/1992 | Rydell et al. . |
| 5,190,541 | 3/1993 | Abele et al. ........................... 606/50 |
| 5,197,964 | 3/1993 | Parins . |
| 5,258,006 | 11/1993 | Rydell et al. . |
| 5,267,998 | 12/1993 | Hagen ................................... 606/50 |
| 5,445,638 | 8/1995 | Rydell et al. ........................... 606/51 |

FOREIGN PATENT DOCUMENTS

| | | |
|---|---|---|
| 0517244A1 | 12/1992 | European Pat. Off. . |
| 0518230A1 | 12/1992 | European Pat. Off. . |
| 2310137 | 12/1976 | France . |
| 2680314A1 | 2/1993 | France . |

OTHER PUBLICATIONS

"Seitzinger Tripolar™ Cutting Forceps"(Brochure 1994): Cabot Technology Corporation p. 1–6.

Primary Examiner—Angela D. Sykes
Assistant Examiner—Michael Peffley

[57] ABSTRACT

A bipolar surgical instrument is disclosed which includes electrical conductors which are separated by an insulating member disposed therebetween, the insulating member having a longitudinally extending bore for reception of a blade member. The blade member is selectively actuatable by a lever member extending from the handle portion of the bipolar surgical instrument.

19 Claims, 7 Drawing Sheets

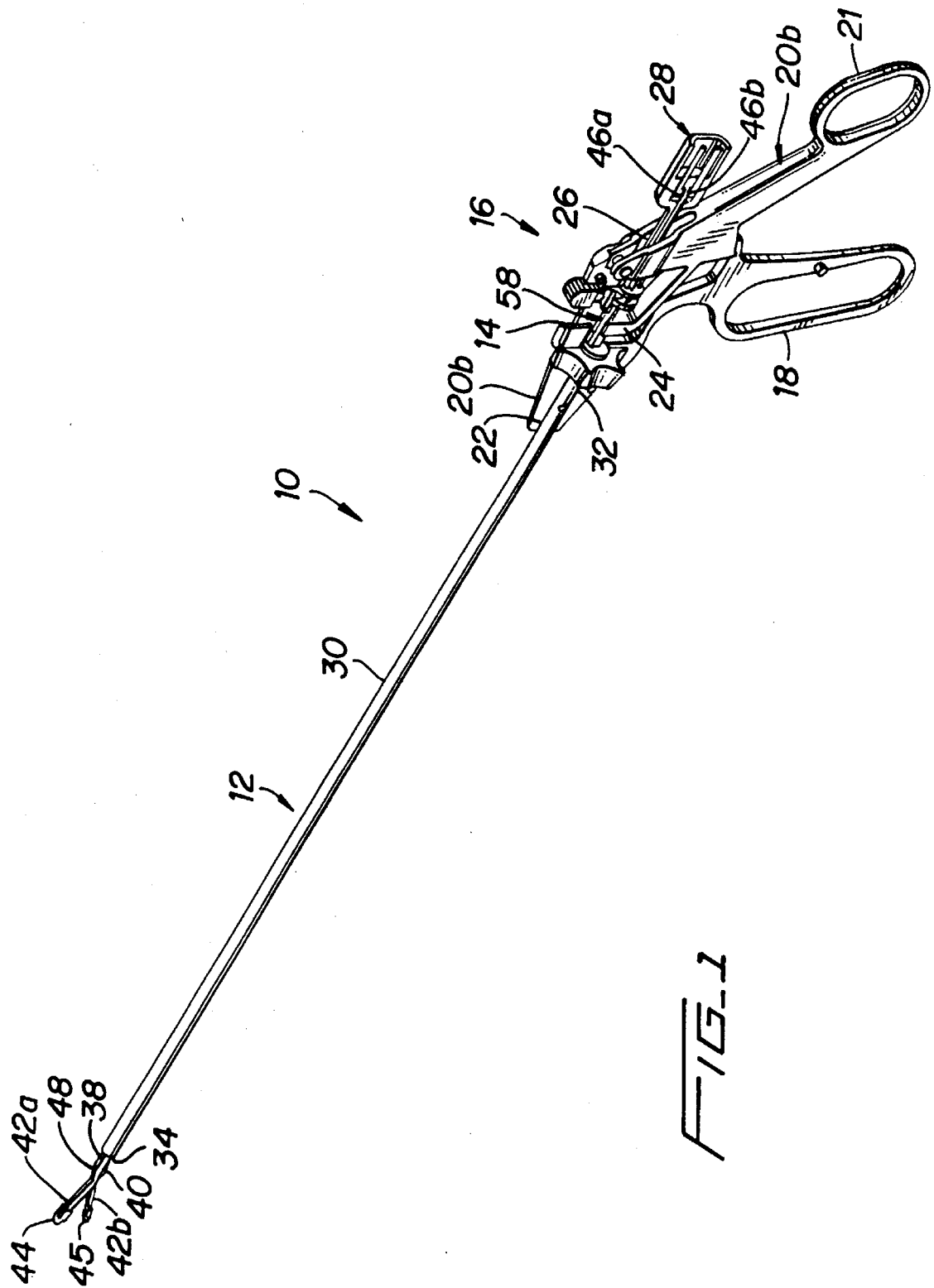
FIG_1

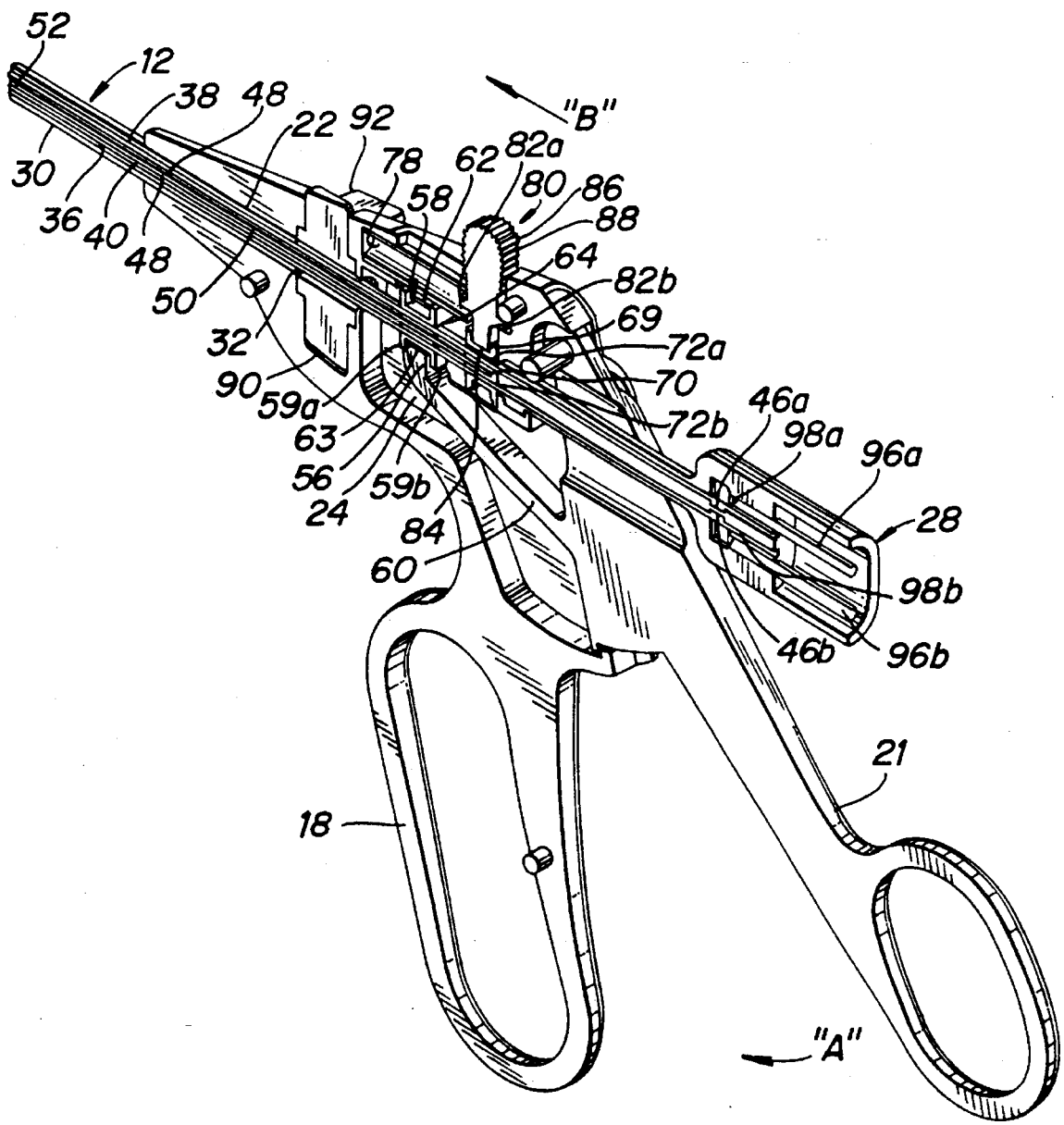
FIG_2A

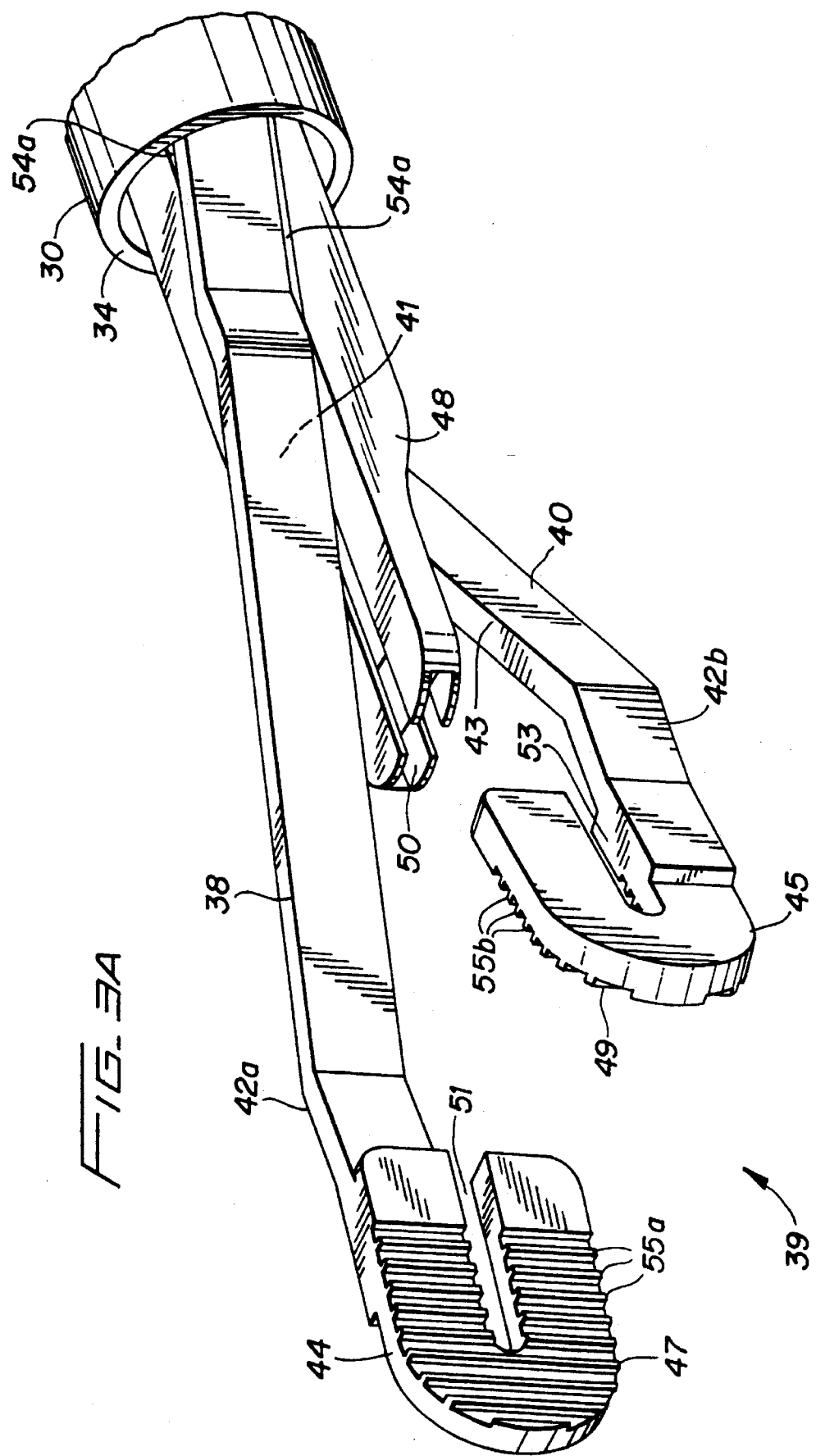

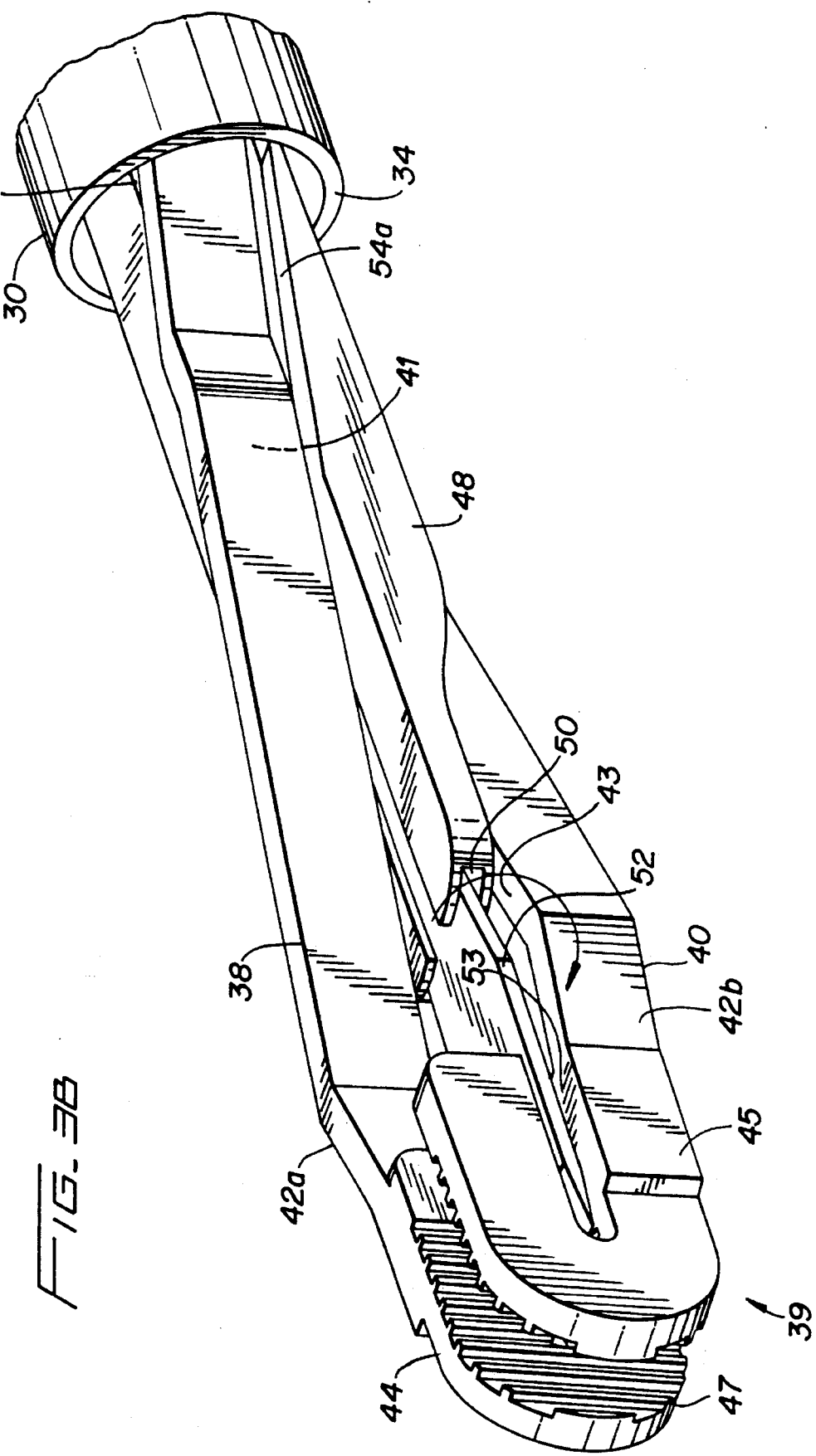

BIPOLAR SURGICAL INSTRUMENT FOR COAGULATION AND CUTTING

BACKGROUND

1. Technical Field

This application relates to bipolar surgical instruments and, more particularly, to bipolar surgical forceps having a cutting blade for selectively grasping, manipulating, cutting and coagulating body tissue.

2. Background of Related Art

Electrocauterization involves the sealing of blood vessels and/or the coagulation of blood and other fluids which are capable of coagulation by the application of a high frequency electrical current. In bipolar electrosurgery, a high frequency power supply is connected to the bipolar instrument and an electrical current is applied through an electrode which contacts the body tissue to be treated. A return electrode is placed in contact with or in close proximity to the current-supplying electrode such that an electrical circuit is formed between the two electrodes. In this manner, the applied electrical current is limited to the body tissue held between the electrodes. Current passing from one electrode to the other produces heat sufficient to seal the blood vessels in tissue or to coagulate blood and other fluids capable of coagulation. Each electrode of the bipolar instrument is electrically isolated within the instrument and is separately connected to the power supply. Typical power supplies such as the SSE2L™ available from Valleylab, Inc. of Boulder, Colo., are r.f. generators which can produce different electrical wavefronts to effect coagulation. When the electrodes are separated from one another, the electrical circuit is open and thus inadvertent contact of body tissue with either of the separated electrodes does not cause current to flow.

Electrosurgical procedures have, in recent years, become increasingly widespread. The ease and speed of coagulating tissue saves the surgeon valuable time while minimizing internal bleeding by the patient. Endoscopic and laparoscopic surgical procedures have created additional incentives for the use of electrosurgical techniques. In laparoscopic procedures, surgery is performed in the interior of the abdomen through a small incision; in endoscopic procedures, surgery is performed in any hollow viscus of the body through narrow tubes inserted through small entrance wounds in the skin. Because laparoscopic and endoscopic surgery does not bring the surgeon into direct contact with the operation site, internal bleeding must be quickly controlled by instruments easily operable from a remote location. Electrosurgical instruments provide the surgeon with the ability to coagulate tissue such that bleeding is minimized and to effectively seal off bleeders during laparoscopic and endoscopic procedures. Because laparoscopic and endoscopic surgery involve instrument manipulation from a remote location, the actuating mechanism must be convenient to operate once the instrument has been properly positioned.

Several configurations have been proposed for bipolar electrosurgical instruments particularly adapted for treating tissue. Bipolar knives are described in U.S. Pat. Nos. 4,161,950 and 4,232,676. In these patents, two or more separated, fixed electrodes are disposed on the surface of a ceramic blade. These electrodes are used to cut and/or coagulate tissue when electrical current passes through tissue positioned between a pair of these fixed electrodes.

Another bipolar electrosurgical instrument is the bipolar forceps. This instrument, examples of which are described in U.S. Pat. Nos. 3,643,663, 4,003,380, 5258,006 and 5,342,359 is used to treat tissue held between the conductive forceps jaws. Current flows through tissue held between the forceps jaws to effect coagulation of the tissue.

Other designs for bipolar forceps have been proposed. In U.S. Pat. No. 5,151,102, a sintered, insulating blood vessel contact member is provided on stainless steel or titanium forceps. Exposed electrodes of a conductive resin are disposed over the surface of the vessel contact member.

The product literature for EVERSHEARS®, available from Everest Medical Corporation, Minneapolis, Minn., describes laparoscopic scissors. Ceramic blades and a single-action dissecting tip are illustrated.

Once the tissue has been coagulated and any bleeders have been effectively sealed off, it is often desired that the tissue so coagulated be severed at the site of the coagulation. Bipolar forceps, while capable of burning through tissue, do not shear the tissue in a clean-cut fashion. Bipolar scissors, on the other hand, while capable of shearing tissue, usually do so at the same time coagulation is occurring, which often results in incomplete coagulation of the tissue. U.S. Pat. No. 5,342,381 to Tidemand describes a combination bipolar scissors and forceps instrument which is capable of performing as both a bipolar forceps and a bipolar scissors. However, when performing as a bipolar scissors it does not eliminate the problem of simultaneous shearing and coagulation. In addition, because the combination scissors and forceps are positioned on the same member, tissue which is not intended to be cut may inadvertently contact the shearing portion of the member.

At present, surgeons who desire to coagulate and cut tissue will usually employ an electrosurgical forceps to coagulate the tissue and then proceed to cut the tissue by utilizing a conventional endoscopic scissors, such as the Endo Shears™ instrument available from United States Surgical Corporation, Norwalk Conn. This requires either the removal of the electrosurgical forceps from the surgical site in order to introduce the endoscopic scissors, or the introduction of the endoscopic scissors through an alternate port, with the surgeon exercising care not to contact the electrically conductive forceps with any conductive portion of the shearing instrument.

A need therefore exists in the art for a bipolar electrosurgical instrument which is capable of first coagulating tissue and then cutting the coagulating tissue without removing the bipolar instrument or inserting additional instrumentation. A need also exists in the art for an improved bipolar electrosurgical instruments in which coagulation and cutting are not simultaneous function, but which may be performed independently of each other with ease.

SUMMARY OF THE INVENTION

The bipolar electrosurgical instrument of the present invention overcomes the disadvantages of previous instruments by employing electrical conductors which are separated by an insulating member disposed therebetween, the insulating member having a longitudinally extending bore for reception of a blade member. The blade member is selectively actuatable by a lever member extending from the handle portion of the bipolar surgical instrument.

BRIEF DESCRIPTION OF THE DRAWINGS

Various embodiments are described herein with reference to the drawings wherein:

FIG. 1 s a reduced perspective view with the left handle portion removed of a bipolar surgical instrument according to the present application.

FIG. 2A is an enlarged partial cross-section of the handle of FIG. 1.

FIG. 3A is an enlarged perspective of the distal end of the instrument of FIG. 1 with the jaws open, blade retracted.

FIG. 3B is an enlarged perspective of the distal end of the instrument of FIG. 1 with the jaws closed with the blade extended.

DETAILED DESCRIPTION OF PREFERRED EMBODIMENTS

Figure 2B:
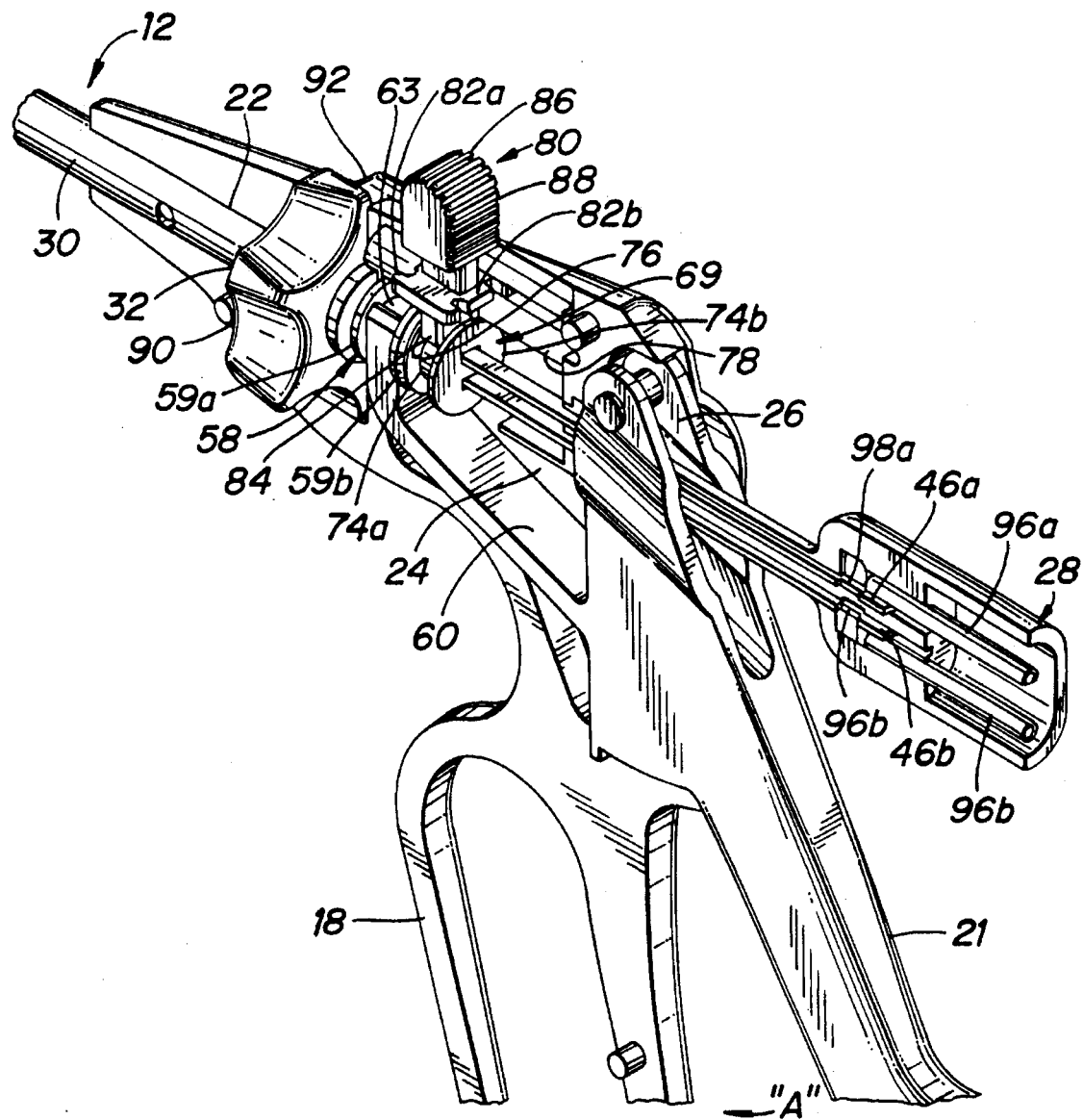
FIG. 2B is an enlarged perspective view with the left handle portion removed of the handle of FIG. 1 with the knob in a distal position.

In the drawings and in the description which follows, the term "proximal", as is traditional, will refer to the end of the apparatus which is closest to the operator, while the term "distal" will refer to the end which is furthest from the operator.

The present apparatus shall be discussed in terms of endoscopic procedures and apparatus. However, use herein of terms such as "endoscopic" and "endoscopically", should not be construed to limit the present application to an apparatus for use only in conjunction with an endoscopic tube. To the contrary, it is believed that the present apparatus may find use in conventional, open surgery as well as procedures where access is limited to a small incision including but not limited to arthroscopic or laparoscopic procedures.

Referring initially to FIG. 1 there is illustrated a bipolar surgical instrument in accordance with the present application which is designated generally by reference numeral 10. Surgical instrument 10 includes elongated endoscopic portion 12 extending from barrel portion 14 of handle assembly 16. Handle assembly 16 further includes stationary grip 18 and pivotable grip 21 extending from barrel portion 14. Handle assembly 16 is formed from complementary left (removed) and right body portions 20a and 20b which when assembled define a bore portion 22 for receiving endoscopic portion 12, an interior cavity 24 for accommodating various components which will be described hereinbelow, and a connection port 26 for receipt of electrical connection member 28.

Referring now to FIGS. 2A–2B in conjunction with FIG. 1, endoscopic portion 12 includes elongated tubular member 30 having a longitudinal axis disposed therethrough. Elongated tubular member 30 has a proximal end 32, a distal end 34 and a lumen 36 extending therebetween. Tubular member 30 is preferably fabricated from a biocompatible, non-conductive material such as a polyester-fiberglass composite which is available from Polygon, a company located in Walkerton Ind. Alternatively, the tubular member may be fabricated from a biocompatible, conductive material such as stainless steel and then coated with an insulating material. Tubular member 30 is received within bore portion 22 and is preferably fixedly attached thereto. Extending longitudinally through lumen 36 of tubular member 30 are electrical conductors 38 and 40. Conductors 38 and 40 are preferably formed from a biocompatible, conductive material such as stainless steel and are electrically isolated from one another by an insulation member 48 disposed therebetween. Conductors 38 and 40 include distal end portions 42a and 42b respectively, which extend from the distal end 34 of tubular member 30, and also include proximal end portions, 46a and 46b which extend through proximal end 32 of tubular member 30 and through handle assembly 16 to contact electrical connection member 28. Referring now to FIGS. 3A-3B, distal end portions 42a and 42b of conductors 38 and 40 include inclined portions 41, 43 respectively which engage camming surfaces 54a, 54b (not shown) formed on insulation member 48. Inclined portions 41, 43 terminate in a tool mechanism 39, preferably comprising forceps jaws 44, 45. Forceps jaws 44, 45 are preferably a "U" shaped configuration and include tissue-gripping surfaces 47, 49 respectively, which have a plurality of serrated edges 55a, 55b for securing tissue therebetween. Forceps jaws 44, 45 further include cooperating slots 51, 53 disposed therethrough for reception of a blade member 52.

Figure 4A:
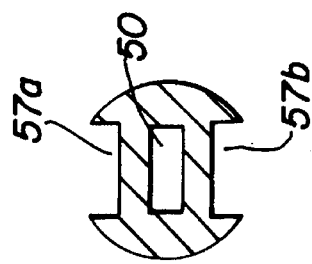
FIG. 4A is in enlarged cross-section of the insulating member of FIG. 1.
Figure 4B:
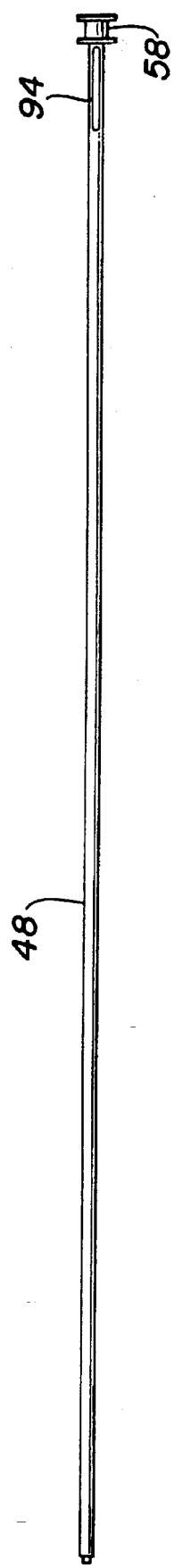
FIG. 4B is a reduced side elevation of the insulating member of FIG. 1.
Figure 5:
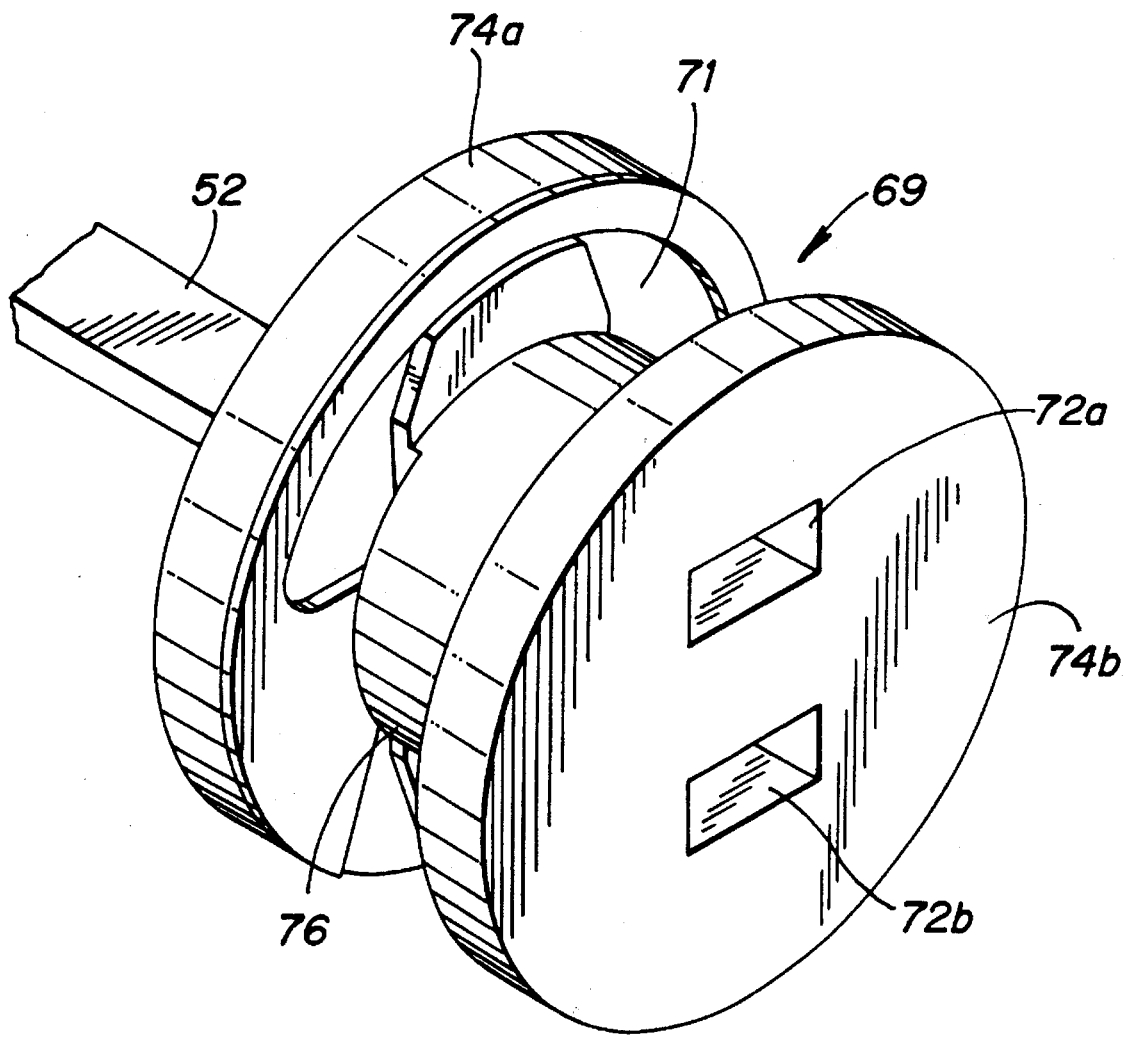
FIG. 5 is a enlarged perspective of the second spool member of FIG. 1.

Referring once again to FIGS. 1–2B, insulation member 48 extends longitudinally within lumen 36 of tubular member 30 and is configured for reciprocating movement therein. Insulation member 48 includes a bore on aperture 50 disposed therethrough for reception of blade member 52. As shown in FIG. 4B, insulation member 48 further includes longitudinally extending slots 57a, 57b for reception of conductors 38 and 40, respectively in order to maintain electrical isolation of conductors 38 and 40 with respect to each other. Proximal end 56 of insulation member 48 extends through bore portion 22 of handle member 16 and into interior cavity 24 where it is received and secured within a first spool member 58 by way of a suitable adhesive, such as biocompatible glue. Conductors 38 and 40 extend through lumen 64 of first spool member 58 and continue through interior cavity 24. First spool member 58 includes generally circular end caps 59a, 9b having a first diameter, a post member 63 of a second diameter which is preferably less than the first diameter, the post member being disposed between end caps 59a, 59b.

With continuing reference to FIGS. 1–2B, pivotable grip 21 includes an actuation arm 60 which is preferably formed integrally therewith and which extends into interior cavity 24. Actuation arm 60 is captured between end caps 59a, 59b such that actuation of pivotable grip 21 toward stationary grip 18 in the direction of arrow "A", causes actuation arm 60 to move distally. Distal movement of actuation arm 60 causes corresponding distal movement of spool member 58 from the position shown in FIG. 2A to the position shown in FIG. 2B. Insulation member 48 is secured within spool member 58, therefore, distal movement of spool member 58 results in corresponding distal movement of insulation member 48. As insulation member 48 is moved distally, camming surfaces 54a, 54b engage inclined portions 41, 43 of electrical conductors 38, 40, respectively. Engagement of inclined portions 41, 43 by camming surfaces 54a, 54b forces forceps jaws 44, 45 into a substantially closed position, as shown in FIG. 3B where tissue-gripping surfaces 47, 49 are disposed substantially parallel to each other.

Referring now to FIGS. 2A–3B, blade member 52 is longitudinally disposed within bore 50 of insulation member 58 and is adapted for reciprocating movement therein. Blade member 52 extends from the proximal end 56 of insulation member 48 and is received and secured within a second spool member 69 by way of a suitable adhesive, such as biocompatible glue and may additionally be secured by an engagement spring 71. Second spool member 69 is adapted for reciprocating movement within interior cavity 24 and includes a slot 70 disposed therein for receipt of blade member 52 and further includes a pair of bores 72a, 72b disposed therethrough for reception of conductors 38 and 40. Second spool member 69 includes generally circular end caps 74a, 74b having a first diameter, a post member 76 of a second diameter which is preferably less than the first diameter, the post member 76 being disposed between end caps 74a, 74b.

With continuing reference to FIGS. 2A–3B, barrel portion 14 further includes a slot 78 disposed therein. An actuation lever 80 having extension arms 82a, 82b preferably formed integrally therewith is slideably disposed within slot 78. Actuation lever 80 further includes a first end 84 which is disposed within interior cavity 24 and is captured between end caps 74a, 74b of second spool member 69, and a second end 86 which includes a gripping surface 88 extending from barrel portion 14. Actuation of gripping surface 88 in the direction of arrow "B" moves actuation lever 80 distally within slot 78 from the position shown in FIG. 2A to the position shown in FIG. 2B. Movement of actuation lever 80 causes corresponding distal movement of second spool member 69 within interior cavity 24. Blade member 52 is secured within second spool member 69, therefore, distal movement of spool member 69 results in corresponding distal movement of blade member 52. As blade member 52 is moved distally it extends from the distal end of insulation member 48 and into cooperating slots 51, 53 of forceps jaws 44, 45 as shown in FIG. 3B.

With continued reference to FIGS. 2A-3B, barrel portion 14 further preferably includes a slot 90 formed therethrough for reception of a knurled rotation knob 92. Rotation knob 92 includes a projection (not shown) which is received within a longitudinal slot 94 disposed adjacent the proximal end of insulation member 48. Rotation of knob 90, therefore results in rotation of insulation member 48 as well as conductors 38 and 40. Bipolar surgical instrument 10 further includes an electrical connection member 28 for connection with an r.f. generator. Conductors 38, 40 are held in electrical contact with connection prongs 96a, 96b by extensions 98a, 98b, respectively.

The operation of bipolar instrument 10 will now be described. Endoscopic portion 12 is inserted into a cannula which is disposed through the abdominal wall of a patient and into the abdominal cavity as is known in the art. Forceps jaws 44, 45 are placed adjacent tissue to be coagulated, and pivotable arm 21 is actuated in the direction of arrow "A" (FIG. 2A) thereby closing the forceps jaws 44, 45 and capturing the tissue to be coagulated therebetween as described hereinabove. Once jaws 44, 45 are closed the surgeon activates a switch or pedal located on the generator to allow current to flow to the bipolar instrument 10. The current is received through electrical connection member 28 and travels through conductors 38, 40 and into forceps jaws 44, 45 as is known in the art to coagulate the tissue. Once the tissue is coagulated, the surgeon once again activates the switch or pedal to stop the current flow to the instrument 10. At this time, if cutting is desired, the surgeon moves actuation lever 80 distally in the direction of arrow "B" (FIG. 2A) to effectuate distal movement of blade member 52 as described hereinabove to cut the tissue. After the tissue has been coagulated and cut, the actuation lever 80 is moved proximally and blade member 52 is moved into its first, retracted position. Lever 80 is preferably spring loaded into the first position by a biasing spring, but alternatively may be moved into the position by manually actuating the lever. Pivotable handle may then be moved into its first position to open jaws 44, 45.

It will be understood that various modifications may be made to the embodiments disclosed herein. For example, forceps jaws 44, 45 although shown as generally "U" shaped could formed in any shape capable of grasping tissue therebetween. Therefore, the above description should not be construed as limiting, but merely as exemplifications of preferred embodiments. Those skilled in the art will envision other modifications within the scope and spirit of the claims appended hereto.

What is claimed is:

1. A bipolar electrosurgical instrument comprising:

a handle assembly;

an endoscopic portion attached to said handle assembly and extending distally therefrom, the endoscopic portion having a lumen extending therethrough defining a longitudinal axis;

an insulating member longitudinally disposed within the lumen of the endoscopic portion and including a bore disposed therethrough;

a pair of conductors disposed within the lumen of the endoscopic portion and separated by the insulating member, the conductors terminating at a distal end in a tool mechanism; and a cutting member disposed within the bore of the insulating member and movable from a first position disposed within the insulating member toward the tool mechanism to a second position at least partially exterior the insulating member.

2. The instrument of claim 1, further comprising an actuation member to move the cutting member between the first and second position.

3. The instrument of claim 2, wherein the actuation member is at least partially received within a spool member.

4. The instrument of claim 1, wherein the tool mechanism comprises a pair of jaws, at least one of the jaws having an elongated slot disposed therein to receive the cutting member when the cutting member is in the second position.

5. The instrument of claim 1, wherein the handle assembly includes a stationary handle and a pivotable handle.

6. The instrument of claim 1 wherein each conductor has a proximal portion extending in general alignment with the lumen and a distal portion extending at an angle to the proximal portion, the direction and angle of the distal portion of each conductor being opposite the direction and angle of the other conductor such that the respective distal portions are in cross-over relation.

7. An endoscopic instrument comprising:

a handle assembly;

an endoscopic portion extending from the handle assembly, the endoscopic portion having a lumen extending therethrough defining a longitudinal axis;

a pair of conductors longitudinally disposed within the lumen of the endoscopic portion and terminating at a distal end in a tool mechanism;

an insulating member longitudinally disposed within the lumen of the endoscopic portion and defining an elongated aperture extending therethrough, the insulating member defining s pair of longitudinally disposed slots for respectively receiving the conductors to electrically isolate one from the other;

a cutting member longitudinally disposed within the elongated aperture of the insulating member, the cutting member being electrically isolated from each of the conductors and being movable between a first position at least partially within the elongated aperture, and a second position toward the tool mechanism and at least partially exterior the insulating member;

an actuation member operative to move the cutting member between the first and second positions.

8. The instrument of claim 7, wherein the conductors terminate at a distal end in a tool mechanism.

9. The instrument of claim 8, wherein the tool mechanism comprises a pair of forceps jaws, at least one of the jaws having a slot formed therethrough.

10. The instrument of claim 9, wherein the first position of the cutting member is substantially within the lumen of the endoscopic portion, spaced from the forceps jaws, and the second position is at least partially received within the slot disposed within at least one of the forceps jaws.

11. The instrument of claim 9, wherein each jaw has a slot formed therethrough, the cutting member being disposed within the slots when actuated to the second position.

12. The instrument of claim 7 wherein a first conductor has a proximal portion extending in general alignment with the lumen and is positioned on one side of the insulating member, the conductor having a distal portion extending at an angle to the proximal portion, and the other conductor is positioned on the opposite side of the insulating member and has a proximal portion extending in general alignment with the lumen and a distal portion extending at an angle to the proximal portion, the angle and direction of each conductor being opposite the angle and direction of the other conductor so that the respective distal portions thereof are respectively in cross-over relation.

13. A bipolar surgical instrument comprising:

a handle assembly;

an endoscopic portion extending from the handle assembly, the endoscopic portion having a lumen extending therethrough defining a longitudinal axis;

a pair of conductors disposed within the lumen of the endoscopic portion and terminating at a distal end in forceps jaws, at least one of the forceps jaws having an elongated slot disposed therein;

an insulating member disposed between the pair of conductors and defining an elongated aperture, the insulating member electrically isolating the pair of conductors from each other;

a cutting member longitudinally disposed within the elongated aperture defined by the insulating member, the cutting member thereby being electrically isolated from each of the conductors and being movable between a first position spaced from the forceps jaws and a second position at least partially disposed within the elongated slot of the at least one forceps jaws; and an actuation member operative to move the cutting member between the first and second positions.

14. The instrument of claim 13, wherein the actuation member is at least partially received within a spool member.

15. The instrument of claim 13, wherein the handle assembly includes a stationary handle and a pivotable handle.

16. The instrument of claim 13 wherein the insulating member defines a pair of slots formed thereon for receiving the conductors and electrically isolating the conductors with respect to each other.

17. The instrument of claim 16, wherein the elongated aperture in the insulating member is a longitudinal slot disposed therethrough, the longitudinal slot receiving the cutting member and electrically isolating the cutting member from the conductors.

18. The instrument of claim 13 wherein a first conductor has a proximal portion extending in general alignment with the lumen and positioned on one side of the insulating member, the conductor having a distal portion extending at an angle to the proximal portion, and the other conductor is positioned on the opposite side of the insulating member and has a proximal portion extending in general alignment with the lumen and a distal portion extending at an angle to the proximal portion, the angle and direction of each conductor being opposite the angle and direction of the other conductor so that the other respective distal portions thereof are respectively in cross-over relation.

19. A bipolar electrosurgical instrument comprising:

a handle assembly;

an endoscopic portion attached to said handle assembly and extending distally therefrom, the endoscopic portion having a lumen extending therethrough and defining a longitudinal axis;

an insulating member longitudinally disposed within the lumen of the endoscopic portion and including an elongated aperture disposed therethrough;

a first conductor having a proximal portion disposed within the lumen and extending in general alignment with the lumen and being positioned on one side of the insulating member in a first slot defined by the insulating member, the first conductor including a distal portion extending in a first direction at an angle to the proximal portion and terminating in a first forceps jaw;

a second conductor having a proximal portion disposed within the lumen and extending in general alignment with the lumen and being positioned in a second slot defined by the insulating member on the opposite side of the insulating member, the second conductor including a distal portion extending in a second direction and at an angle to the proximal portion and terminating in a second forceps jaw, the angle and direction of the distal portion of the second conductor being substantially equal and opposite the angle and direction of the distal portion of the first conductor so as to position the first and second forceps jaws in respective opposed relation; and a cutting member disposed within the elongated aperture of the insulating member and movable from a first position disposed within the insulating member in a direction toward the forceps jaws to a second position at least partially exterior the insulating member.

\* \* \* \* \*